US00PP23996P2

(12) United States Plant Patent
van Noort

(10) Patent No.: US PP23,996 P2
(45) Date of Patent: Oct. 15, 2013

(54) ***ECHINACEA* PLANT NAMED 'SUMMER SALSA'**

(50) Latin Name: *Echinacea purpurea*
Varietal Denomination: Summer Salsa

(76) Inventor: Marco van Noort, Warmond (NL)

( * ) Notice: Subject to any disclaimer, the term of this patent is extended or adjusted under 35 U.S.C. 154(b) by 80 days.

(21) Appl. No.: 13/385,943

(22) Filed: Mar. 14, 2012

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Annette Para
(74) *Attorney, Agent, or Firm* — Penny J. Aguirre

(57) ABSTRACT

A new cultivar of hybrid *Echinacea*, 'Summer Salsa', characterized by its anemone-type (semi-double) inflorescences with ray florets and disk florets that open orange-red in color and become deep orange, its stems that are strong and held upright, its floriferous habit, and its compact and short plant habit.

2 Drawing Sheets

Botanical classification: *Echinacea purpurea.*
Variety denomination: 'Summer Salsa'.

BACKGROUND OF THE INVENTION

The present Invention relates to a new and distinct cultivar of *Echinacea purpurea* and will be referred to hereafter by its cultivar name, 'Summer Salsa'. 'Summer Salsa' represents a new coneflower, an herbaceous perennial grown for landscape use.

The new cultivar arose from an ongoing breeding program conducted by the Inventor in a designated field at his nursery in Warmond, The Netherlands. The goal of his breeding program is to create new cultivars of *Echinacea* that exhibit a short and firm plant habit combined with inflorescences with attractive form and coloration. The Inventor made a cross in summer of 2009 between unnamed proprietary plants of *Echinacea purpurea* from his breeding line. 'Summer Salsa' was selected by the Inventor as a single unique plant amongst the resulting seedlings from the above cross in September of 2010.

Asexual reproduction of the new cultivar was first accomplished by division in Warmond, The Netherlands in 2010 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Summer Salsa' as a unique cultivar of *Echinacea.*

1. 'Summer Salsa' exhibits a compact and short plant habit.
2. 'Summer Salsa' exhibits strong, upright stems.
3. 'Summer Salsa' is very floriferous.
4. 'Summer Salsa' exhibits anemone-type inflorescences (semi-double): disk florets exhibit an enlarged petal.
5. 'Summer Salsa' exhibits inflorescences with ray florets and disk florets that open orange-red in color and become deep orange.

The female parent differs from 'Summer Salsa' in having weaker stems and in having single inflorescences. The male parent differs from 'Summer Salsa' in having a less compact and taller plant habit, in having weaker stems, and in having inflorescences that are less intense in color. 'Summer Salsa' can be most closely compared to the cultivars 'Irresistible' (U.S. Plant Pat. No. 20,756), 'Hot Papaya' (U.S. Plant Pat. No. 21,022) 'Eccentric' (U.S. Plant patent application Ser. No. 13/385,810), 'Piccolino' (U.S. Plant Pat. No. 23,348). All are similar to 'Summer Salsa' in having inflorescences that are semi-double inflorescences. 'Irresistible' differs from 'Summer Salsa' in having inflorescences that are more pink orange. 'Hot Papaya' differs from 'summer Salsa' in being taller in height and in having flowers that are more red in color. 'Eccentric' differs from 'summer Salsa' in having inflorescences that emerge red-purple before turning to reddish-orange. 'Piccolino' differs from 'Summer Salsa' in having inflorescences that are red-purple in color.

BRIEF DESCRIPTION OF THE DRAWING

The plants and plant parts in the accompanying photographs depict a six month-old plant of 'Summer Salsa' as field grown outdoors in Warmond (containerized for the photographs), The Netherlands.

The photograph in FIG. 1 provides a side view of 'Summer Salsa' in bloom.

Figure 1:
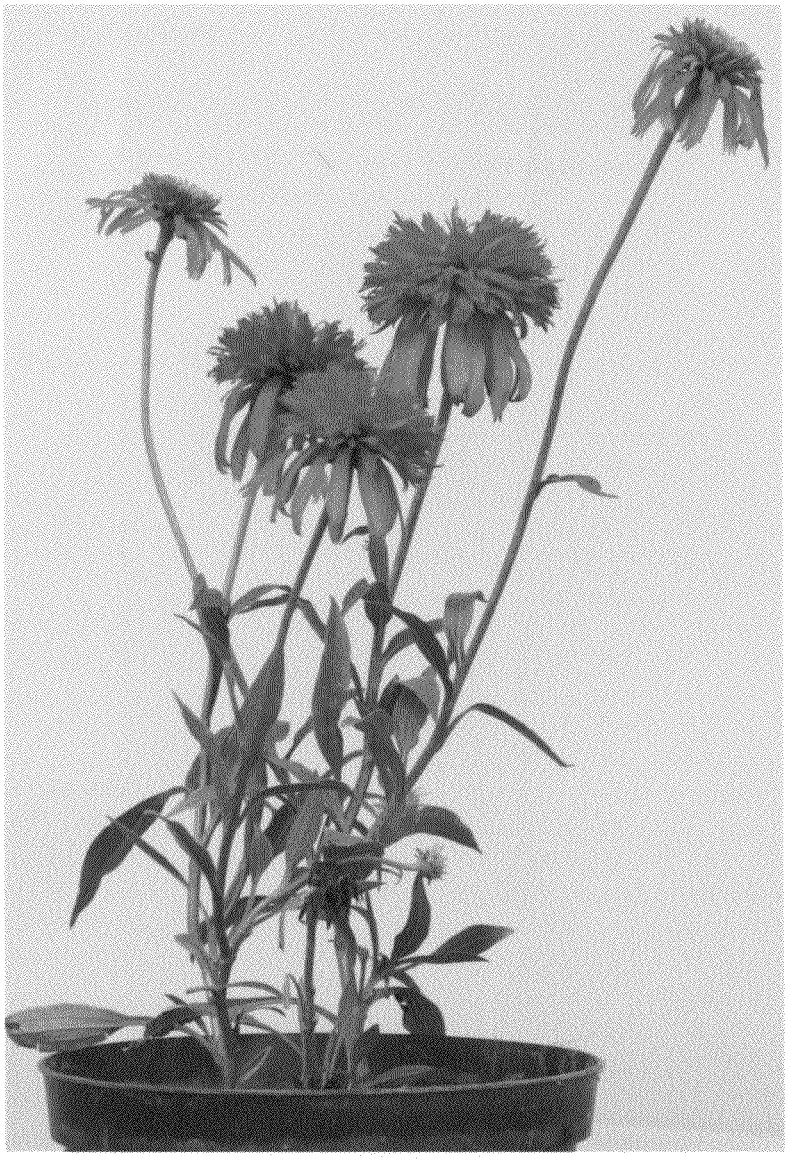
Figure 2:
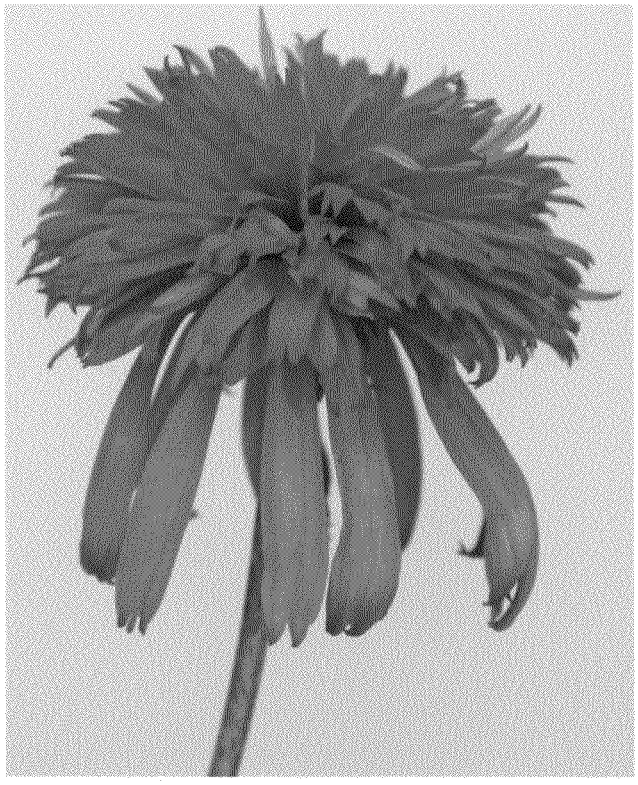

The photograph in FIG. 2 shows a close-up of an inflorescence of 'Summer Salsa'.

Figure 3:
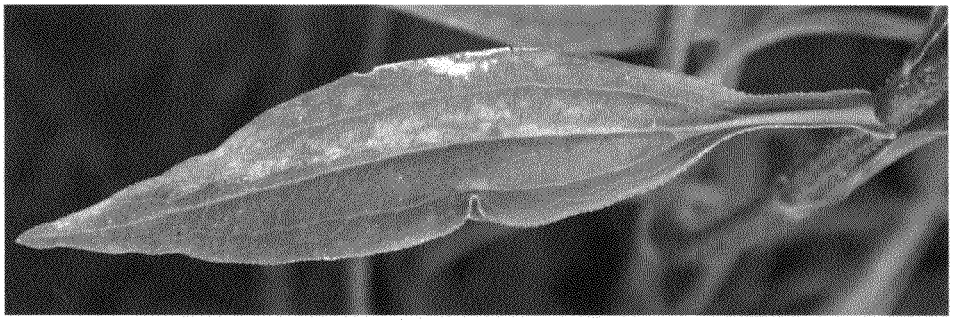

The photograph in FIG. 3 provides a close-up view of a leaf of 'Summer Salsa'.

The Colors in the photograph may differ slightly from the color values cited in the detailed botanical description, which accurately describe the colors of the new *Echinacea.*

BOTANICAL DESCRIPTION OF THE PLANT

The following is a detailed description of six-month-old plants of the new cultivar as grown outdoors in a test garden in Warmond, The Netherlands. The plants were grown under average day temperatures of 14° to 28° C. and average night temperatures of 6° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from early July to late September in The Netherlands.

*Plant habit.*—Herbaceous perennial, clump forming, upright.

*Height and spread.*—Reaches about 45.8 cm in height 39 cm in spread.

*Hardiness.*—U.S.D.A. Zones 3 to 4.

*Diseases resistance.*—Not more susceptible to pests/diseases than other *Echinacea* varieties.

*Root description.*—Fibrous.

Growth and propagation:

*Propagation.*—Division, vegetative stem cuttings, and tissue culture.

*Growth rate.*—Low to moderately vigorous.

Stem description:

*Shape.*—Rounded.

*Stem color.*—144A to 144B, marbled with 146A.

*Stem size.*—An average of 5 mm in diameter and 19.9 cm in length (from base of plant to base of uppermost leaf).

*Stem strength.*—Strong.

*Stem aspect.*—Held upright, stems grow in an average angle of 45° from the base.

*Stem surface.*—Moderately rough to touch and sparsely covered with very short strigose hairs about 0.4 mm in length and 157D in color.

*Stem number.*—Average of 4 main stems.

*Internode length.*—Average of 3.3 cm in length.

*Branching.*—Main flowering stem grows from base.

Foliage description:

*Leaf shape.*—Narrow ovate to narrow elliptic.

*Leaf division.*—Simple.

*Leaf base.*—Attenuate.

*Leaf apex.*—Narrow acute.

*Leaf venation.*—Pinnate, color: upper surface; 146C, lower surface; 146C to 146D.

*Leaf margins.*—Entire.

*Leaf attachment.*—Petiolate.

*Leaf arrangement.*—Alternate.

*Leaf size.*—Average of 7.4 cm in length and 2.0 cm in width.

*Leaf color.*—Young upper surface; between 137A and 143A, young lower surface; 137C, mature upper surface; 146A, mature lower surface; 146B.

*Leaf surface.*—Upper and lower surface is moderately glossy, and sparsely covered with short strigose hairs about 0.3 mm in length and 157D in color.

*Petioles.*—Upper stem leaves nearly sessile, average of 1.8 cm in length, 3 mm in height, 4 mm in width, upper surface; 145A, becoming darker at the margins; 146A in color, lower surface; 144C, becoming darker at the margins; 146B in color, upper and lower surfaces are smooth.

Flower description:

*Type.*—Terminal capitulum, heterogamous with ray florets around the head margin and disk florets with expanded ray floret-like petal, anemone-type (referred to as semi-double).

*Capitulum number.*—An average of 1 per stem.

*Lastingness of inflorescence.*—About 2 to 3 weeks.

*Capitulum size.*—Matures to about 8.8 cm in height and 8.3 cm in diameter, disk is about 8.3 cm in diameter.

*Fragrance.*—Faint, sweet fragrance.

*Involucral bracts or phyllary.*—About 45 arranged in 3 overlapping rows, average of 1.0 cm in length and 3 mm in width, cuneate base, acute apex, narrow ovate in shape, upper surface; 143A in color, lower surface; 143A to 143B in color, margins entire and sparsely covered with short hairs about 0.3 mm in length and 155C in color, upper surface is smooth, lower surface is smooth and covered with very short hairs average length 0.2 mm, 157D in color.

*Buds.*—Flattened globular in shape, immature ray florets near vertical (upright), an average of 1.8 cm in length and 2.5 cm in diameter, color; 146A, immature ray florets; 145A.

*Peduncle.*—Strong, terminal is an average of 15.1s cm in length and 4 mm in diameter with axillary peduncles, terminals held upright with axillary peduncle held at an average angle of 25° to vertical, color; 144B, marbled with 146A, surface is sparsely covered with short strigose hairs about 0.5 mm in length and 157D in color.

*Ray florets.*—Rotate, average of 11 per inflorescence, oblanceolate to narrow oblanceolate in shape, upper surface; smooth and velvety, slightly ribbed lengthways (carinate), lower surface; smooth, moderately ribbed lengthways (carinate), about 6.4 cm in length and 1.0 cm in width, praemorse apex, cuneate base, entire margin, strongly drooping in an average angle of about 40° downward from horizontal, color of upper surface when opening; 169A, color of lower surface when opening; 180C, tinged 145C at the tip, color of upper surface when fully open; 169A, color of lower surface when fully open; 180C to 180D, non fading.

*Disk flowers* (*bisexual*).—Numerous, about 160, arranged spirally on disc, apex is praemorse, narrow cuneate base, entire margin, average of 3.5 cm in length and 7 mm in width, upper surface is smooth, dull and velvety, lower surface is smooth, dull and slightly glossy, color when opening upper surface; N25A to N25B, color of lower surface when opening; 180C with the base tinged 145C, color of upper surface when fully open; 169A with the tip becoming between N30A and 42A, color of lower surface when fully open; 180C.

*Disk spines.*—Average of 160, acicular in shape, acute apex, attenuate base, smooth and glossy surface, color is 46A at apex, 21A in mid region and 144A to 144B at base.

*Receptacle.*—Triangular in shape, an average of 10 mm in height and 7 mm in diameter, and 155C in color.

Reproductive organs (present on disk florets only):

*Gynoecium.*—Pistil; 1, 7 mm in length, style; about 5.5 mm in length and N34C in color, stigma; unequal, decurrent and 46A in color, ovary; 145D in color.

*Androcoecium.*—Stamens; 4, filaments; 2 mm in length and N200B in color, anthers; linear in shape, about 2 mm in length and N170A in color, pollen; none observed.

*Fruit/seed.*—No seed production has been observed.

It is claimed:

1. A new and distinct cultivar of *Echinacea* plant named 'Summer Salsa' substantially as herein illustrated and described.

* * * * *